United States Patent
Büttner et al.

[11] 3,979,411
[45] Sept. 7, 1976

[54] 2-TRIFLUOROMETHYLIMINO-BENZO-HETEROCYCLIC COMPOUNDS

[75] Inventors: Gerhard Büttner, Cologne; Erich Klauke, Odenthal-Hahnenberg; Paul-Ernst Frohberger, Leverkusen; Ingeborg Hammann, Cologne, all of Germany

[73] Assignee: Bayer Aktiengesellschaft, Leverkusen, Germany

[22] Filed: Jan. 30, 1975

[21] Appl. No.: 545,657

Related U.S. Application Data

[62] Division of Ser. No. 344,800, March 26, 1973, Pat. No. 3,884,931.

[30] Foreign Application Priority Data

Apr. 15, 1972 Germany............................ 2218329

[52] U.S. Cl. ......................... 260/327 M; 260/340.5
[51] Int. Cl.² .............. C07D 317/66; C07D 339/06; C07D 327/04
[58] Field of Search .................... 260/327 M, 340.5

[56] References Cited
UNITED STATES PATENTS

| | | |
|---|---|---|
| 2,851,391 | 9/1958 | Gevjovich et al. ................... 167/33 |
| 3,770,769 | 11/1973 | Schneider ...................... 260/327 M |
| 3,884,931 | 5/1975 | Buttner et al. ................... 260/307 D |

*Primary Examiner*—Natalie Trousof
*Assistant Examiner*—C. M. S. Jaisle
*Attorney, Agent, or Firm*—Burgess, Dinklage & Sprung

[57] ABSTRACT

2-Trifluoromethylimino-benzo-heterocyclic compounds of the general formula

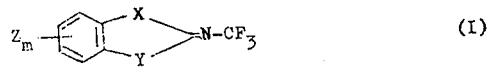

(I)

in which
X is oxygen or sulfur,
Y is oxygen, sulfur or the radical

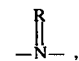

R is lower alkyl, cycloalkyl, aryl, aryl substituted by at least one of halogen, nitro, methyl and methoxy, alkylcarbalkoxy with up to 6 carbon atoms, alkylsulfonyl, arylsulfonyl, dialkylamidosulfonyl, or —CO—R',
R' is alkyl or alkoxy with up to 12 carbon atoms, aryl, amino, lower alkylamino, di-lower alkylamino, or arylamino, each Z independently is halogen, trifluoromethyl, nitro, lower alkyl, lower alkoxy, di-lower alkylamino, acyl with up to 6 carbon atoms, a sulfonic acid group, a sulfonic acid amide group, or a sulfonic acid amide group substituted by alkyl with up to 6 carbon atoms, and
m is an integer from 0 to 4,
which possess fungicidal, insecticidal and acaricidal properties, and a process for their preparation wherein a compound of the general formula

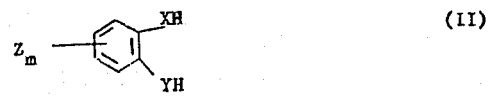

(II)

is reacted with perfluoroazapropene of the formula

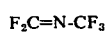

(III)

in an aprotic solvent in the presence of a hydrogen fluoride acceptor.

6 Claims, No Drawings

2-TRIFLUOROMETHYLIMINO-BENZO-HETEROCYCLIC COMPOUNDS

This is a division of application Ser. No. 344,800, filed Mar. 26, 1973, now U.S. Pat. No. 3,884,931.

The present invention relates to and has for its objects the provision of particular new 2-trifluoromethylimino-benzo-heterocyclic compounds which possess fungicidal, insecticidal and acaricidal properties, active compositions in the form of mixtures of such compounds with solid and liquid dispersible carrier vehicles, and methods for producing such compounds and for using such compounds in a new way especially for combating pests, e.g. fungi, insects and acarids, with other and further objects becoming apparent from a study of the within specification and accompanying examples.

2-Trifluoromethylimino derivatives of heterocyclic five-membered rings with a fused benzene nucleus have not hitherto been disclosed.

The present invention provides 2-trifluoromethylimino derivatives of heterocyclic compounds with five-membered rings, of the general formula

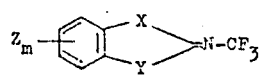
(I)

in which
X is oxygen or sulfur,
Y is oxygen, sulfur or the radical

R is lower alkyl, cycloalkyl, aryl, aryl substituted by at least one of halogen, nitro, methyl and methoxy, alkylcarbalkoxy with up to 6 carbon atoms, alkylsulfonyl, arylsulfonyl, dialkylamidosulfonyl, or —CO—R',
R' is alkyl or alkoxy with up to 12 carbon atoms, aryl, amino, lower alkylamino, di-lower alkylamino, or arylamino, each Z independently is halogen, trifuloromethyl, nitro, lower alkyl, lower alkoxy, di-lower alkylamino, acyl with up to 6 carbon atoms, a sulfonic acid group, a sulfonic acid amide group, or a sulfonic acid amide group substituted by alkyl with up to 6 carbon atoms, and
m is an integer from 0 to 4.
When Y is

R preferably is methyl, ethyl, cyclohexyl, phenyl, chlorophenyl, nitro-phenyl or lower alkylcarbo-lower alkoxy with up to 4 carbon atoms in each alkyl group, or methanesulfonyl, ethanesulfonyl, p-toluene-sulfonyl or dimethylaminosulfonyl, or the acyl group —CO—R', wherein R' is alkyl or alkoxy with up to 8 carbon atoms, or phenyl, lower alkylamino or di-lower alkylamino, each with up to 4 carbon atoms in each alkyl moiety.

Z preferably is chlorine, trifluoromethyl, nitro, alkyl with up to 4 carbon atoms, the sulfonic acid group or the sulfonamide, N-methyl-sulfonamido or N,N-dimethylsulfonamido radical. Preferably $m$ is 0, 1, 2 or 4.

The invention also provides a process for the production of a compound of formula (I) in which a compound of the general formula

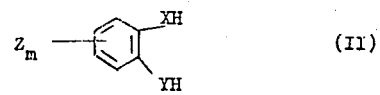
(II)

in which
X, Y, Z and m have the abovementioned meanings, is reacted with perfluoroazapropene of the formula

(III)

or a secondary product thereof as indicated below, in an aprotic solvent, in the temperature range of about 0° to 100°C, in the presence of a hydrogen fluoride acceptor.

It is very surprising that the abovementioned compounds of the formula (II) give, when reacted with perfluoroazapropene of the formula (III), in a single reaction and in satisfactory yield, the previously unknown five-membered rings of the formula (I). It is furthermore surprising that the compounds according to the invention possess fungicidal, acaricidal and insecticidal activity. A technical advance has been achieved by the discovery of this new category of compounds having interesting properties, and of the unusual process for their production.

It is noteworthy that in formula (II) even if Y is —NR— X cannot also be —NR—, i.e. the starting material cannot be an o-phenylenediamine. Such diamines do not react in the same way, i.e. they do not undergo ring closure in accordance with the present invention. Furthermore, they are unstable in the presence of acids and undergo polymerization.

If o-(N-acetyl)-aminophenol and perfluoroazapropene are used as the starting compounds and sodium fluoride as the acid-binding agent, the course of the reaction can be represented by the following equation:

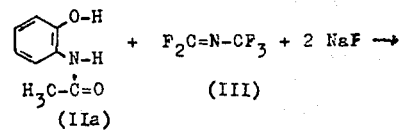

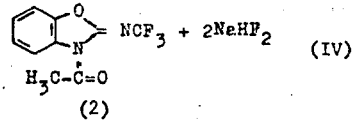
(2)

The compounds of the formula (II) to be used as starting substances are known and may be prepared according to a known process as described for example in:

Helvetica Chim. Acta 22, 92 (1939); U.S. Pat. No. 2,795,610; J. Amer. Soc. 51, 2763; Liebigs Ann. Chem. 738, 192 (1970)).

As examples of compounds of the general formula (II) there may be mentioned: pyrocatechol; 5-tert.-butylpyrocatechol; perchloropyrocatechol; o-phenylenedithiol; perchlorophenylenedithiol; 4-methyl-o-phenylenedithiol, o-(N-methyl-amino)-thiophenol; 5-nitro-2-(methyl-amino)-thiophenol, o-(N-methylamino)-phenol; 5-chloro-2-(N-methylamino)-phenol, o-(N-phenylamino)-phenol; o-(N-2',4'-dinitrophenylamino)-phenol; 4-chloro-2-(N-carbethoxymethyl)-aminophenol; o-(N-acetyl)-aminophenol; 4-methyl-2-(N-acetylamino)-phenol; 2-(N-acetylamino)-4-(methylamino-sulfonyl)-phenol; o-(N-benzoyl)-aminophenol; o-[N-(2,5-dichlorobenzoyl)]-aminophenol; o-[N-(3-trifluoro-methylbenzoyl)]-aminophenol; o-[N-(4-tert.-butylbenzoyl)]-aminophenol, o-(N-carbomethoxy)-aminophenol; 3,5-dichloro-2-(N-carbethoxy)-aminophenol; 4-nitro-6-chloro-2-(N-carbomethoxy)-aminophenol; o-(N-dimethylaminocarbonyl)-aminophenol; 4-chloro-5-nitro-2-(N-di-methylaminocarbonyl)-aminophenol; 4-nitro-2-(N-methylaminocarbonyl)-aminophenol; 4-nitro-2-[N-(n-butylaminocarbonyl)]-aminophenol; 4-chloro-2-(N-methylaminocarbonyl)-aminophenol; o-(N-methyl sulfonyl)-aminophenol, o-[N-(n-butyl sulfonyl)]-aminophenol; 4-acetyl-2-(ethylsulfonyl)-aminophenol; o-(N-tosyl)-aminophenol; o-[N-(3'-nitro-phenylsulfonyl)]-aminophenol; o-[N-(3'-chloro-4'-methylphenylsulfonyl)]-aminophenol; and o-(N-dimethyl(-aminosulfonyl)-aminophenol.

The perfluoroazapropene of the formula (III) to be used as a starting substance is also known, being disclosed in Chem. Review 65, 387 (1965) and J. Chem. Ing. Data 10, 398 (1965)).

As solvents it is generally possible to use aprotic substances such as chlorinated hydrocarbons, for example methylene chloride, chloroform or chlorobenzene, or aromatic hydrocarbons, for example benzene or toluene), but preferably dipolar aprotic solvents such as acetonitrile, acetone, dimethylformamide, sulfolane and dimethylsulfoxide. An "aprotic solvent" is defined as a diluent which does not contain an ionizable proton in the molecule (Römpp, "Chemie-Lexikon", page 217, Franck'sche Verlagsbuchhandlung, Stuttgart (1972), and also Chem. Review 69, page 1–32 (1969)).

As acceptor for the hydrogen fluoride produced in the reaction it is possible to use a tertiary amine, such as triethylamine or dimethylaniline, but it is preferrred to use an alkali metal fluoride, such as sodium fluoride or potassium fluoride.

The reaction temperaures can be varied over a wide range. In general, the reaction is carried out at about 0° to 100°C, preferably at about 20° to 80°C.

The process according to the invention can for example be carried out by dissolving a molar equivalent of the starting material of formula (II) in acetonitrile, dimethylformamide or toluene, adding about 2 molar equivalents of dry sodium fluoride, an progressively introducing about 1 to 1.5 molar equivalents, preferably about 1.2 molar equivalents, of perfluoroazapropene, for example from a steel cylinder, into the resulting suspension, in the temperature range indicated above, while stirring. After completion of the reaction, the mixture may be stirred further for a short time, the precipitated sodium hydrogen fluoride may be filtered off and the solvent may be concentrated in vacuo. The crystalline crude product which remains is in many cases sufficiently pure, or it can be easily purified by recrystallization.

According to a special embodiment of the invention it is possible to use the perfluoroazapropene (III), in the form of an addition product thereof, namely bis-(trifluoromethyl)-amine (IV) which may be produced by addition of hyrogen fluoride to (III), and N,N,N'-tris(trifluoromethyl)-fluoroformamidine (V), which may be produced by dimerization of (III), i.e. addition to itself. The process can in this way be carried out more easily because preparation of pure perfluoroazapropene can be dispensed with and because the compounds mentioned, of the respective formulae $(CF_3)_2NH$ and $(CF_3)_2N—CF=N—CF_3$
(IV) (V)

can be added dropwise as liquids, because of their higher boiling points.

The active compounds according to the invention display a strong fungitoxic action. They do not appear to harm crop plants in the concentrations required to combat fungi, and they have a low toxicity to warm-blooded animals. For these reasons they are suitable for use as plant protection agents for combating fungi. Fungitoxic agents are employed in plant protection for combating Archimvcetes, Phycomycetes, Ascomycetes, Basidiomycetes and *Fungi Imperfecti*.

The active compounds according to the invention have a broad spectrum of action and can be employed against parasitic fungi which attach above-ground parts of plants, or attack the plants through the soil, and also against seedborne causative organisms of diseases.

The compounds possess a good action against *Fusicladium dendriticum*, the causative organism of apple scab, against *Podosphaera leucotricha*, the causative organism of powdery mildew of apples, against *Helminthosporium gramineum*, the causative organism of stripe disease of barley, and against *Tilletia caries*, the causative organism of bunt of wheat.

However, the compounds according to the invention are also active against other fungi which attack rice plants or other crop plants, such as *Mycosphaerella musicola*, *Verticillium alboartrum*, *Phialophora cinerescene* and varieties of Fusarium.

The compounds according to the invention are distinguished by a good activity and a broad spectrum of action against phytopathogenic soil fungi and against seed-borne fungal diseases of plants. They can suitably be used as soil treatment agents and seed dressings, and are in many cases superior to customary commercially available preparations.

The compounds according to the invention furthermore possess an insecticidal and acaricidal activity. They may be successfully employed in plant protection for combating harmful sucking and biting insects, Diptera and mites (Acarina), also in the veterinary and hygiene fields, and furthermore in the protection of stored products against a large number of animal pests (endoparasites and ectoparasites).

To the sucking insects there belong, in the main, aphids (Aphidae) such as the green peach aphid (*Myzua persicae*), the bean aphid (*doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*, the rosy apple aphid (*Sappaphis mali*), the mealy plum aphid (*Hyalopterus arundinis*) and the cherry blackfly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelia bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*) the ermine moth (*Hyponomeuta padella*), the Mediterranean flour moth (*Ephestia kuhniella*) and greater wax moth (*Galleria mellonella*).

With the mites (Acari) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithrodorus moubata*).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.) amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solids and/or liquid dispersible carrier vehicles and/or with other known compatible active agents, especially plant protection agents, such as other fungicides, insecticides and acaricides, or rodenticides, nematocides, herbicides, fertilizers growth-regulating agents, etc., if desired, or in the form of particular dosage preparations for specific application made therefrom, such as solutions, emulsions, suspensions, powders, pastes and granules, which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

For soil treatment, amounts of active compound of 1 to 500 g per $m^3$ of soil, preferably 10 to 200 g, are generally required.

In the treatment of seed, amounts of active compound of 0.01 to 50 g per kg of seed, preferably 0.1 to 5 g, are in general required for application as seed dressings.

Furthermore, the present invention contemplates methods of selectively killing, combating or controlling pests, e.g. fungi, insects and acarids, which comprises applying to at least one of correspondingly (a) such fungi, (b) such insects, (c) such acarids, and (d) the corresponding habitat thereof, i.e. the locus to be protected, a correspondingly combative or toxic amount, i.e. a fungicidally, insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

*Podosphaera* test (powdery mildew of apples)/Protective

Solvent: 4.7 parts by weight of acetone
Emulsifier: 0.3 part by weight of alkylarylpolyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (*Podosphaera leucotricha* Salm.) and placed in a greenhouse at a temperature of 21° – 23°C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following Table:

Table 1

*Podosphaera* test /protective

| Active compound | | Infection in % of the infection of the untreated control at an active compound concentration (in % by weight) of 0.025% |
|---|---|---|
| $CH_3\!\!-\!\!N(CH_3)\!\!-\!\!C(=\!S)\!\!-\!\!S\!\!-\!\!S\!\!-\!\!C(=\!S)\!\!-\!\!N(CH_3)\!\!-\!\!CH_3$ | (known) (A) | 29 |
| dichlorobenzoxazoline =NCF$_3$, N-C(=O)OC$_2$H$_5$ | (15) | 4 |
| chlorobenzoxazoline =NCF$_3$, N-C(=O)-NH-CH$_3$ | (19) | 11 |

EXAMPLE 2

*Fusicladium* test (apple scab) / Protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated with an aqueous conidium suspension of the apple scab causative organism (*Fusicladium dendriticum* Fuckel) and incubated for 18 hours in a humidity chamber at 18° – 20°C and at a relative atmospheric humidity of 100%.

The plants then again came into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 2

*Fusicladium* test/protective

| Active compound | | Infection in % of the infection of the untreated control at an active compound concentration (in % by weight) of 0.0062% |
|---|---|---|
| (CH₃)₂N-C(=S)-S-S-C(=S)-N(CH₃)₂ (known) | (A) | 31 |
| benzoxazine with N-CF₃ and SO₂-CH₃ | (1) | 1 |
| benzoxazine with N-CF₃ and COO-CH₃ | (14) | 0 |
| benzoxazine with =NCF₃ and O₂S-C₆H₄-CH₃ | (20) | 0 |
| dichloro-benzoxazine with =NCF₃ and C(=O)OC₂H₅ | (15) | 0 |
| chloro-benzoxazine with =NCF₃ and O=C-N(H)-CH₃ | (19) | 0 |

EXAMPLE 3

Agar plate test

Test for fungitoxic effectiveness and breadth of the activity spectrum.

Solvent: Acetone
Parts by weight: a. 1,000
 b. 100

To produce a suitable preparation of the active compound, 1 part by weight of the active compound was taken up in the stated amount of solvent.

The preparation of the active compound was added to potato dextrose agar (which had been liquefied by heating) in such an amount that the desired concentration of active compound was set up therein. After thorough shaking to achieve a uniform dispersion of the active compound, the agar was poured into Petri dishes under sterile conditions. When the mixture of substrate and active compound had solidified, test fungi from pure cultures were inoculated onto it in small discs of 5 mm diameter. The Petri dishes remained at 20°C for 3 days for incubation.

After this time, the inhibiting action of the active compound on the mycelium growth was determined in categories, taking into account the untreated control. 0 means no mycelium growth, either on the treated substrate or on the inoculum; the symbol — means mycelium growth on the inoculum only, no spread to the treated substrate; and the symbol + means mycelium growth from the inoculum onto the treated substrate, similar to the spread to the untreated substrate of the control.

The active compounds, the concentration of the active compounds, the test fungi and the inhibition effects achieved can be seen from the following table:-

Table 3

Agar plate test

| Active compound | | Active compound concentration in the substrate, in mg per liter | Corticium rolfsii | Sclerotinia sclerotiorum | Verticillium alboatrium | Thielaviapsis basicola | Phytophthora cactorum | Fusarium culmorum | Fusarium oxysporum | Fusarium solani f. pisi |
|---|---|---|---|---|---|---|---|---|---|---|
| Untreated | | — | + | + | + | + | + | + | + | + |
| CH₂-NH-C(=S)-S\\Zn / CH₂-NH-C(=S)-S (known) | (A) | a) 10  b) 100 | + 0 | + + | + + | + + | + 0 | + — | + 0 | + + |
| benzoxazine =N-CF₃ | (5) | a) 10  b) 100 | 0 0 | 0 0 | 0 0 | 0 0 | 0 0 | 0 0 | 0 0 | 0 0 |
| (CH₃)₃C-benzoxazine =N-CF₃ | (4) | a) 10  b) 100 | 0 0 | 0 0 | + + | 0 0 | 0 0 | 0 0 | + + | + + |

Table 3-continued

| Active compound | | Agar plate test Active compound concentration in the substrate, in mg per liter | Corti- cium rolfsii | Sclero- tinia sclero- tiorum | Verti- cillium albo- atrium | Thiela- viapsis basi- cola | Phyto- phthora cactorum | Fusa- rium cul- morum | Fusa- rium oxy- sporum | Fusarium solani f. pisi |
|---|---|---|---|---|---|---|---|---|---|---|
| 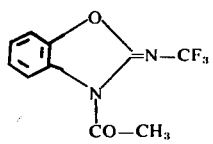 | (2) | a  10<br>b  100 | 0<br>0 | 0<br>0 | 0<br>0 | 0<br>0 | 0<br>0 | 0<br>0 | 0<br>0 | 0<br>0 |
| 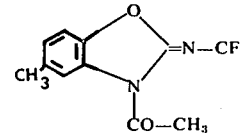 | (11) | a  10<br>b  100 | 0<br>0 | 0<br>0 | 0<br>0 | —<br>— | +<br>0 | —<br>0 | +<br>0 | —<br>0 |
| 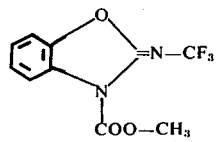 | (14) | a  10<br>b  100 | 0<br>0 | 0<br>0 | +<br>0 | +<br>— | +<br>0 | 0<br>0 | +<br>0 | +<br>0 |

EXAMPLE 4

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following Table:

Table 4

| Active compound | Seed dressing test/bunt of wheat Active compound concentration in the dressing, in % by weight | Amount of dressing used in g/kg of seed | Spore germination in % |
|---|---|---|---|
| without dressing | — | — | >10 |
| 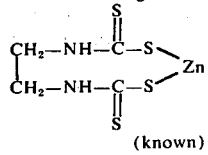 (known) | 10 | 1 | 5 |
| 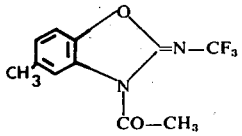 (11) | 10 | 2 | 0.005 |
| 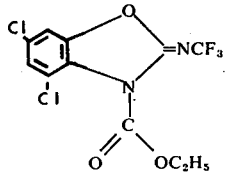 (15) | 10 | 2 | 0.005 |

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, exposed to optimum germination conditions for the spores for 10 days at 10°C in a refrigerator.

EXAMPLE 5

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4°C for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18°C in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentration of the active compounds in the dressing, the amounts of dressing used and the number of diseased plants can be seen from the following Table:

by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table:

Table 6

| | Tetranychus test, resistant | |
|---|---|---|
| Active compound | Active compound concentration in % by weight | Degree of destruction in % after 2 days |
| 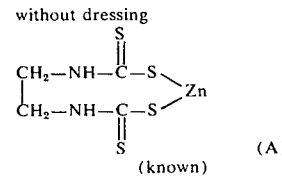 | 0.1 | 0 |
| 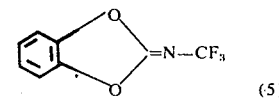 (known) (B) (2) | 0.1 | 100 |

Table 5

| | Seed dressing test/stripe disease of barley | | |
|---|---|---|---|
| Active compound | Active compound concentration in the dressing, in % by weight | Amount of dressing used, in g/kg of seed | Number of plants with stripe disease, in % of the total number of emerged plants |
| without dressing | — | — | 41.3 |
| 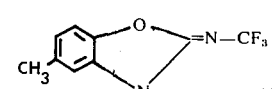 (known) (A) | 30 | 2 | 38.1 |
| 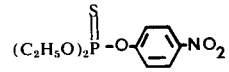 (5) | 30 | 2 | 0.0 |
| 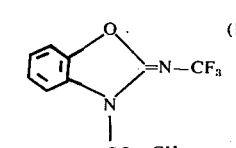 (11) | 30 | 2 | 4.1 |

EXAMPLE 6

Tetranychus test, resistant
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10 to 30 cm, were sprayed with the preparation of the active compound until dripping wet. These bean plants were heavily infested with the two-spotted spider mite or bean spider mite (*Tetranychus urticae*) in all stages of development.

After the specified periods of time, the effectiveness of the preparation of active compound was determined

| | | |
|---|---|---|
| 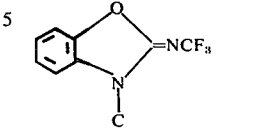 (11) | 0.1 | 100 |
| 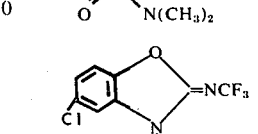 (16) | 0.1 | 100 |
| 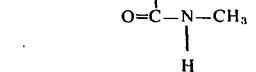 (19) | 0.1 | 100 |
| | 0.01 | 70 |

Table 6-continued

| Active compound | Tetranychus test, resistant | |
|---|---|---|
| | Active compound concentration in % by weight | Degree of destruction in % after 2 days |
| 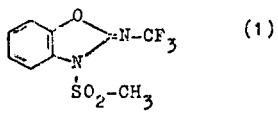 COO—CH₃ (14) | 0.1 | 100 |
| =NCF₃ (15) Cl, Cr, OC₂H₅ | 0.1<br>0.01 | 99<br>50 |

The following examples illustrate the synthesis of the compounds.

EXAMPLE 7

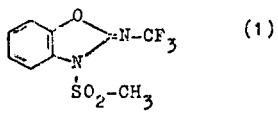

(1)

38 g (0.2 mole) of 2-(N-methylsulfonyl)-aminophenol were partially dissolved in 100 ml of dry acetonitrile, 17 g (0.405 mole) of dry sodium fluoride were added and 30 g (0.22 mole) of perfluoroazapropene were slowly introduced into this suspension at room temperature, while stirring. In the course thereof, the starting material dissolved. After the introduction had been completed, the mixture was stirred for about a further 15 minutes and filtered, and the solvent was concentrated in vacuo. The crude product was recrystallized from methanol. 36 g of 2-trifluoromethylimino-3-methylsulfonyl-benzoxazoline were obtained as colorless crystals of melting point 142°–146°C. The yield of pure material was 64% of theory.

EXAMPLE 8

(2)

15 g (0.1 mole) of 2-(N-acetylamino)-phenol in 100 ml of dry acetonitrile and 9 g (0.214 mole) of dry sodium fluoride were heated to 75°–80°C while stirring and 15 g (0.11 mole) of perfluoroazapropene were slowly passed into this suspension. After completion of the reaction, the mixture was filtered, the solvent was concentrated and the residue was recrystallized from chloroform. 15 g of 2-trifluoromethylimino-3-acetyl-benzoxazoline were obtained as pale yellow prisms of melting point 140°–143°C. The yield of pure material was 67% of theory.

EXAMPLE 9

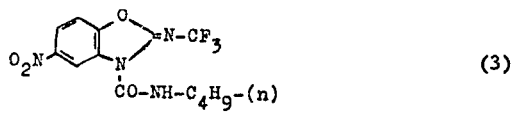

(3)

24 g (0.1 mole) of 2-N-(n-butylaminocarbonyl)-4-nitroaminophenol were dissolved in 70 ml of dry dimethylformamide, 8 g (0.19 mole) of dry sodium fluoride were added and 15 g (0.11 mole) of perfluoroazapropene were slowly introduced at room temperature, while stirring. After completion of the reaction, the mixture was filtered and ice water was carefully added to the reaction solution, while stirring, until no further product precipitated. The precipitate which had formed was filtered off and recrystallized from isopropanol. 21 g of 2-trifluoromethylimino-3-(n-butylaminocarbonyl)-5-nitro-benzoxazoline were obtained as colorless crystals of melting point 121°–122°C. The yield of pure material was 61% of theory.

EXAMPLE 10

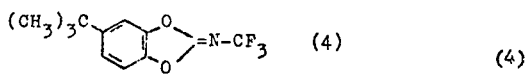

(4)

17 g (0.1 mole) of 4-tert.-butyl-pyrocatechol were dissolved in 100 ml of dry toluene, 9 g (0.214 mole) of dry sodium fluoride were added and 15 g (0.11 mole) of perfluoroazapropene were slowly introduced into this suspension at room temperature, while stirring. After completion of the introduction, the mixture was filtered, the reaction solution was concentrated in vacuo and the solid residue was recrystallized from methanol. 12 g of 2-trifluoromethylimino-5-tert.-butyl-benzdioxol were obtained as colorless crystals of melting point 78°–80°C. The yield of pure material was 47% of theory.

EXAMPLE 11

The compounds listed below were prepared by methods analogous to those of the above Examples 7 to 10.

| Formula | Melting point in °C | Appearance |
|---|---|---|
| =NCF₃ (5) | 56–58 | colorless crystals |

-continued
| Formula | | Melting point in °C | Appearance |
|---|---|---|---|
| 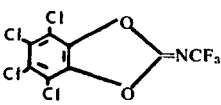 | (6) | 112–115 | colorless crystals |
| 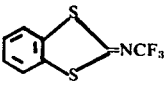 | (7) | 55–60 | yellow crystals |
| 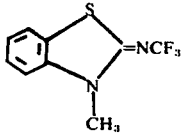 | (8) | 87–89 | " |
| 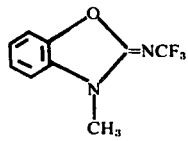 | (9) | 114–116 | red needles |
| 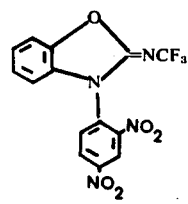 | (10) | 98–100 | brown crystals |
| 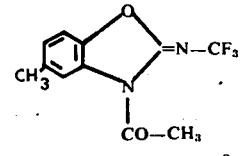 | (11) | 118–121 | " |
| 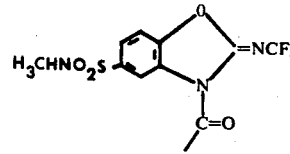 | (12) | 170–175 | colorless crystals |
| 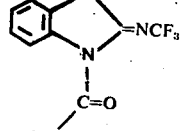 | (13) | 155–157 | pale yellow crystals |
| 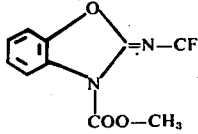 | (14) | 138–140 | colorless crystals |
| 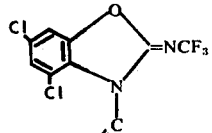 | (15) | 165–166 | " |
| 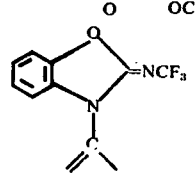 | (16) | 114–115 | " |

| Formula | | Melting point in °C | Appearance |
|---|---|---|---|
| 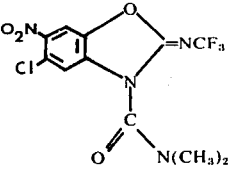 | (17) | 150–155 | yellow crystals |
| 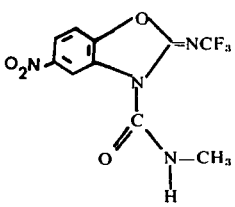 | (18) | 168 (decomposition) | " |
| 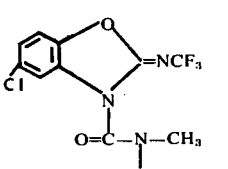 | (19) | 140–142 | yellow crystals |
| 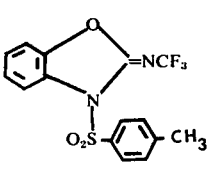 | (20) | 125–130 | colorless crystals |
| 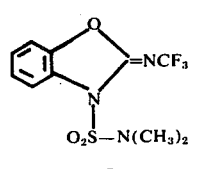 | (21) | 139–140 | " |
| 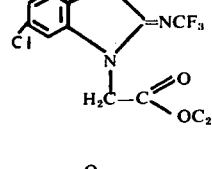 | (22) | 154–155 | " |
| 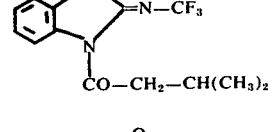 | (23) | 66–69 | colorless needles |
| 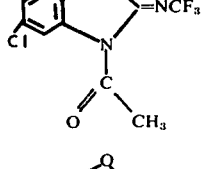 | (24) | 127–130 | colorless needles |
| 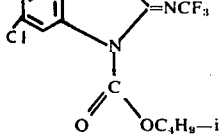 | (25) | 80–84 | colorless needles |

| Formula | Melting point in °C | Appearance |
|---|---|---|
| 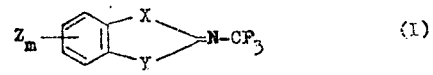 (26) | 98–100 | colorless needles |

Other compounds which can be similarly prepared include:
2-trifluoromethylimino-benzthioxol
2-trifluoromethylimino-3-ethanesulfonyl-benzoxazoline
2-trifluoromethylimino-3-ethyl-5-bromo-benzoxazoline
2-trifluoromethylimino-3-cyclohexyl-6-trifluoromethyl-benzoxazoline
2-trifluoromethylimino-3-phenyl-4-isopropoxy-benzoazoline
2-trifluoromethylimino-3-(4'-chlorophenyl)-5-diethylamino-benzoxazoline
2-trifluoromethylimino-3-(4'-methylphenyl)-5-acetyl-benzoxazoline
2-trifluoromethylimino-3-(3'-ethoxyphenyl)-6-sulfo-benzoxazoline
2-trifluoromethylimino-3-carbonamido-7-sulfonamido-benzoxazoline
2-trifluoromethylimino-3-anilidocarbonyl-6-dimethylamidosulfonyl-benzoxazoline
and the like.

The following example illustrates the synthesis of a starting product of the general formula (II):

144 g (1 mole) of 4-chloro-2-aminophenol (technical product) were dissolved in 300 ml of acetone and simultaneously at a temperature of −5° to +10°C 80 g (1 mole) pyridine and 140 g (1 mole) chloro-formic acid i-butyl ester were added dropwise within 1 hour, while stirring. After the addition has been completed, the mixture was stirred at room temperature for about a further 30 minutes and subsequently poured with stirring into 1.5 l of water. The precipitate has been filtered with suction and dried. 240 g of 4-chloro-2-(N-carbonyl-1-butoxy)-aminophenol were obtained as light brown crystals of melting point 118°–122°C. The Yield was 98% of theory. (The product thus obtained as described is the starting material for compound (25)).

It will be appreciated that the instant specification and examples are set forth by way of illustration and not limitation and that various modifications and changes may be made without departing from the spirit and scope of the present invention.

What is claimed is:

1. A 2-trifluoromethylimino benzoheterocyclic compound with five-members in the heterocyclic ring of the formula

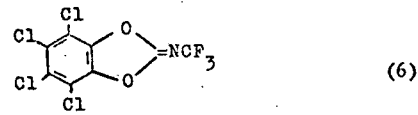

in which
X is oxygen or sulfur,
Y is oxygen or sulfur and
m is an integer from 0 to 4.

2. A compound according to claim 1 in which Z is chlorine or lower alkyl, and m is 0, 1, 2 or 4.

3. A compound according to claim 1 in which said compound is 2-trifluoromethylimino-4,5,6,7-tetrachlorobenzdioxol of the formula

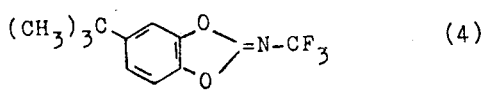

4. A compound according to claim 1 in which said compound is

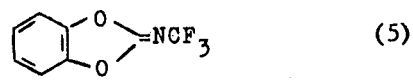

5. A compound according to claim 1 in which said compound is

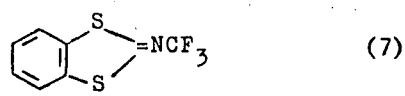

6. A compound according to claim 1 in which said compound is

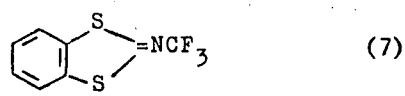

* * * * *

UNITED STATES PATENT OFFICE
CERTIFICATE OF CORRECTION

Patent No. 3,979,411    Dated    September 7, 1976

Inventor(s) Gerhard Buttner et al.

It is certified that error appears in the above-identified patent and that said Letters Patent are hereby corrected as shown below:

Col. 1, line 63    cancel "dimethylaminosulfonyl" and substitute -- dimethylamidosulfonyl --.

Col. 3, line 54    cancel "an" and substitute -- and --.

Col. 4, line 2    cancel "hyrogen" and substitute -- hydrogen --

Col. 4, line 21    cancel "Archimvcetes" and substitute -- Archimycetes --.

Col. 4, 39    cancel "cinerescene" and substitute -- cinerescens --.

Col. 4, line 57    cancel "Muzua" and substitute --Muzus --.

UNITED STATES PATENT OFFICE
CERTIFICATE OF CORRECTION

Patent No. 3,979,411                     Dated September 7, 1976

Inventor(s) Gerhard Buttner et al.

It is certified that error appears in the above-identified patent and that said Letters Patent are hereby corrected as shown below:

Col. 9, line 68       cancel "[structure with (CH₃)₃C-benzene-O-N=N—CF₃ (4)]"

substitute -- [structure with (CH₃)₃C-benzene with two O groups =N—CF₃ (4)] --.

Col. 21, line 26      cancel "benzoazoline" and substitute -- benzoxazoline --.

Col. 22, line 27      Before "and" insert -- each Z independently is halogen or lower alkyl --.

Signed and Sealed this

Seventeenth Day of May 1977

[SEAL]

Attest:

RUTH C. MASON
*Attesting Officer*

C. MARSHALL DANN
*Commissioner of Patents and Trademarks*